(12) United States Patent
Rothenberg

(10) Patent No.: US 8,030,003 B2
(45) Date of Patent: Oct. 4, 2011

(54) DIAGNOSIS OF EOSINOPHILIC ESOPHAGITIS BASED ON PRESENCE OF AN ELEVATED LEVEL OF EOTAXIN-3

(75) Inventor: Marc Elliot Rothenberg, Cincinnati, OH (US)

(73) Assignee: Children's Hospital Medical Center, Cincinnati, OH (US)

( * ) Notice: Subject to any disclaimer, the term of this patent is extended or adjusted under 35 U.S.C. 154(b) by 893 days.

(21) Appl. No.: 11/721,127

(22) PCT Filed: Dec. 7, 2005

(86) PCT No.: PCT/US2005/044456
§ 371 (c)(1),
(2), (4) Date: Jun. 7, 2007

(87) PCT Pub. No.: WO2006/083390
PCT Pub. Date: Aug. 10, 2006

(65) Prior Publication Data
US 2009/0233275 A1 Sep. 17, 2009

Related U.S. Application Data

(60) Provisional application No. 60/633,909, filed on Dec. 7, 2004.

(51) Int. Cl.
*G01N 33/53* (2006.01)
(52) U.S. Cl. .................. 435/7.1; 435/7.9; 435/7.92
(58) Field of Classification Search .................. None
See application file for complete search history.

(56) References Cited

U.S. PATENT DOCUMENTS

| 6,403,782 B1 | 6/2002 | Luster et al. |
| 6,780,973 B1 | 8/2004 | Luster et al. |

FOREIGN PATENT DOCUMENTS

| EP | 0949271 A1 | 10/1999 |
| WO | 2005/106492 A2 | 11/2005 |

OTHER PUBLICATIONS

Shinkai et al (Protein Engineering (2002) vol. 15, p. 923-929).*
Blanchard, C., et al., "Inhibition of Human Interleukin-13-Induced Respiratory and Oesophageal Inflammation by Anti-Human-Interleukin-13 Antibody (CAT-354)," Clin Exp Allergy, 2005, vol. 35, pp. 1096-1103.
Elsner, Jörn, et al., "The CC Chemokine Antagonist Met-RANTES Inhibits Eosinophil Effector Functions Through the Chemokine Receptors CCR1 and CCR3," European Journal of Immunology, 1997, vol. 27, pp. 2892-2898.
Faubion, William A., Jr., et al., "Treatment of Eosinophilic Esophagitis with Inhaled Corticosteroids," Journal of Pediatric Gastroenterology and Nutrition, 1998, vol. 27, pp. 90-93.
Garrett, Jennifer K., et al., "Anti-Interleukin-5 (Mepolizumab) Therapy for Hypereosinophilic Syndromes," J Allerby Clin Immunol, 2004, vol. 113, No. 1, pp. 115-119.
Hogan, S. P., et al., "Review Article: The Eosinophil as a Therapeutic Target in Gastrointestinal Disease," Aliment Pharmacol Ther, 2004, vol. 20, pp. 1231-1240.
Kledal, Thomas N., et al., "A Broad-Spectrum Chemokine Antagonist Encoded by Kaposi's Sarcoma-Associated Herpesvirus," Science, 1997, vol. 277, pp. 1656-1659.
Komiya, Akiko, et al., "Concerted Expression of Eotaxin-1, Eotaxin-2, and Eotaxin-3 in Human Bronchial Epithelial Cells," Cellular Immunology, 2003, vol. 225, pp. 91-100.
Mishra, Anil, et al., "An Etiological Role for Aeroallergens and Eosinophils in Experimental Esophagitis," The Journal of Clinical Investigation, 2001, vol. 107, pp. 83-90.
Naya, Akira, et al., "Discovery of a Novel CCR3 Selective Antagonist," Bioorganic & Medicinal Chemistry Letters, 2001, vol. 11, pp. 1219-1223.
Naya, Akira, et al., "Structure-Activity Relationships of 2-(Benzothiazolylthio)acetamide Class of CCR3 Selective Antagonist," Chem. Pharm. Bull., 2003, vol. 51, No. 6, pp. 697-701.
Proudfoot, Amanda E. I., et al., "Amino-terminally Modified RANTES Analogues Demonstrate Differential Effects on RANTES Receptors," The Journal of Biological Chemistry, 1999, vol. 274, No. 45, pp. 32478-32485.
Sabroe, Ian, et al., "A Small Molecule Antagonist of Chemokine Receptors CCR1 and CCR3," The Journal of Biological Chemistry, 2000, vol. 275, No. 34, pp. 25985-25992.
Saeki, Toshihiko, et al., "Identification of a Potent and Nonpeptidyl CCR3 Antagonist," Biochemical and Biophysical Research Communications, 2001, vol. 281, pp. 779-782.
Teitelbaum, Jonathan E., et al., "Eosinophilic Esophagitis in Children: Immunopathological Analysis and Response to Fluticasone Propionate," Gastroenterology, 2002, vol. 122, pp. 1216-1225.
Varnes, Jeffrey G., et al., "Discovery of N-propylurea 3-benzylpiperidines as Selective CC Chemokine Receptor-3 (CCR3) Antagonists," Bioorganic & Medicinal Chemistry Letters, 2004, vol. 14, pp. 1645-1649.
Wacker, Dean A., et al., "CCR3 Antagonists: A Potential New Therapy for the Treatment of Asthma. Discovery and Structure-Activity Relationships," Bioorganic & Medicinal Chemistry Letters, 2002, vol. 12, pp. 1785-1789.
Whites, John R., et al., "Identification of Potent, Selective Nonpeptide CC Chemokine Receptor-3 Antagonist That Inhibits Eotaxin-, Eotaxin-2-, and Monocyte Chemotactic Protein-4-Induced Eosinophil Migration," The Journal of Biological Chemistry, 2000, vol. 275, No. 47, pp. 36626-36631.
Zimmerman, Nives, et al., "Chemokines in Asthma: Cooperative Interaction Between Cemokines and IL-13," J. Allergy Clin Immunol, 2003, vol. 111, No. 2, pp. 227-242.
International Search Report received in connection with PCT/US2005/044456, Dec. 7, 2006, pp. 1-7.

* cited by examiner

*Primary Examiner* — Prema Mertz
(74) *Attorney, Agent, or Firm* — Davis Wright Tremaine LLP

(57) ABSTRACT

Eotaxin-3, as a marker for eosinophilic esophagitis and methods of assessing, mitigating, and monitoring eosinophilic esophagitis by altering eotaxin-3 and/or CCR3 function, are disclosed.

7 Claims, 2 Drawing Sheets

DIAGNOSIS OF EOSINOPHILIC ESOPHAGITIS BASED ON PRESENCE OF AN ELEVATED LEVEL OF EOTAXIN-3

RELATED APPLICATION

This application claims priority from U.S. Provisional Application Ser. No. 60/633,909 filed Dec. 7, 2004.

The U.S. Government has a paid-up license in this invention and the right in limited circumstances to require the patent owner to license others on reasonable terms as provided for by the terms of Grant No. 2R01 AI045898-05 awarded by the National Institutes of Health.

FIELD OF THE INVENTION

The invention is directed generally to mitigating eosinophilic esophagitis via eotaxin-3.

BACKGROUND

Patients with eosinophilic esophagitis may have symptoms that include abdominal pain, difficulty swallowing, vomiting, failure to thrive and weight loss. In addition, allergy, particularly food allergy, is an associated finding in most patients, and many have concomitant asthma or other chronic respiratory disease. Diagnosis requires endoscopy, and diseased issue shows characteristic punctate white surface dots associated with erythema, loss of vascular pattern, ulcers, or ringed trachea-like appearance.

Patients with eosinophilic esophagus typically have elevated levels of eosinophils in esophageal tissue and peripheral blood. Eosinophils are one type of granulocytic leukocyte (white blood cell) or granulocyte that normally appears in the peripheral blood at a concentration of about 1-3% of total leukocytes. Their presence in tissues is normally primarily restricted to the gastrointestinal mucosa, i.e. the stomach and intestines. Eosinophil accumulation in the peripheral blood and tissues is a hallmark feature of an allergic response, and may cause potent pro-inflammatory effects or tissue remodeling. Because eosinophilic esophagitis is marked by infiltration of eosinophils, this condition may be linked to allergen exposure. Eosinophil accumulation occurs in other allergic diseases such as allergic rhinitis, asthma, and eczema as well as parasitic infections, certain types of malignancies, chronic inflammatory disorders such as inflammatory bowel disease, specific syndromes such as eosinophilic gastroenteritis, eosinophilic colitis, eosinophilic cellulitis, eosinophilic fascitis, and systemic diseases such as Churg Strauss syndrome, eosinophilic pneumonia, and the idiopathic hypereosinophilic syndrome.

Numerous mediators have been identities as eosinophil chemoattractants. These include diverse molecules such as lipid mediators (platelet activating factor (PAF), leukotrienes) and chemokines such as the eotaxin subfamily of chemokines. Chemokines are small secreted proteins produced by tissue cells and leukocytes that regulate leukocyte homing during homeostatic and inflammatory states. Two main subfamilies (CXC and CC chemokines) are distinguished depending upon the arrangement of the first two cysteine amino acids, either separated by one amino acid (CXC), or adjacent (CC).

Due to the increasing incidence of eosinophilic esophagitis, methods to mitigate eosinophilic esophagitis would be beneficial. In addition, because eosinophilic esophagitis is often confused with other disorders such as gastroesophageal reflux disease (GERD), but does not typically respond to anti-GERD therapy, it is important to develop diagnostic features that distinguish between eosinophilic esophagitis and GERD. Diagnosis currently requires endoscopy with subsequent biopsy and analysis of the excised tissue, so that less invasive methods of diagnosing eosinophilic esophagitis would also be beneficial.

SUMMARY OF THE INVENTION

One embodiment of the invention is a method of assessing eosinophilic esophagitis in a patient by comparing the patient's blood concentration of eotaxin-3 to a normal concentration of eotaxin-3, where an increased concentration of eotaxin-3 indicates eosinophilic esophagitis.

Another embodiment of the invention is a diagnostic assay for eosinophilic esophagitis. One embodiment of the assay may include a test strip containing an anti-eotaxin-3 antibody and at least one reagent that indicates binding of the anti-eotaxin-3 antibody to eotaxin-3 present in a supranormal level in a biological sample. Detection may be by visual inspection for a chromogen, fluorogen, colloidal gold agglutination, luminescence, etc.

Another embodiment of the invention is a diagnostic method for eosinophilic esophagitis where eotaxin-3 DNA, eotaxin-3 mRNA, and/or eotaxin-3 protein is present over a normal amount in a patient tissue, as an indicator of eosinophilic esophagitis in the patient.

Another embodiment of the invention is a diagnostic method for eosinophilic esophagitis where a frequency of single nucleotide polymorphisms (SNPs) in the eotaxin-3 gene above normal frequency is an indicator of eosinophilic esophagitis or a marker of disease risk, prognosis, and/or a response to therapy.

Another embodiment of the invention is a method to mitigate eosinophilic esophagitis by providing an inhibitor to eotaxin-3 and/or a receptor, such as CCR3, for binding eotaxin-3 in a cell, such as a mast cell or an eosinophil, under conditions sufficient to inhibit eotaxin-3 binding to the receptor.

These and other advantages will be apparent in light of the following figures and detailed description.

DETAILED DESCRIPTION

Figure 1:
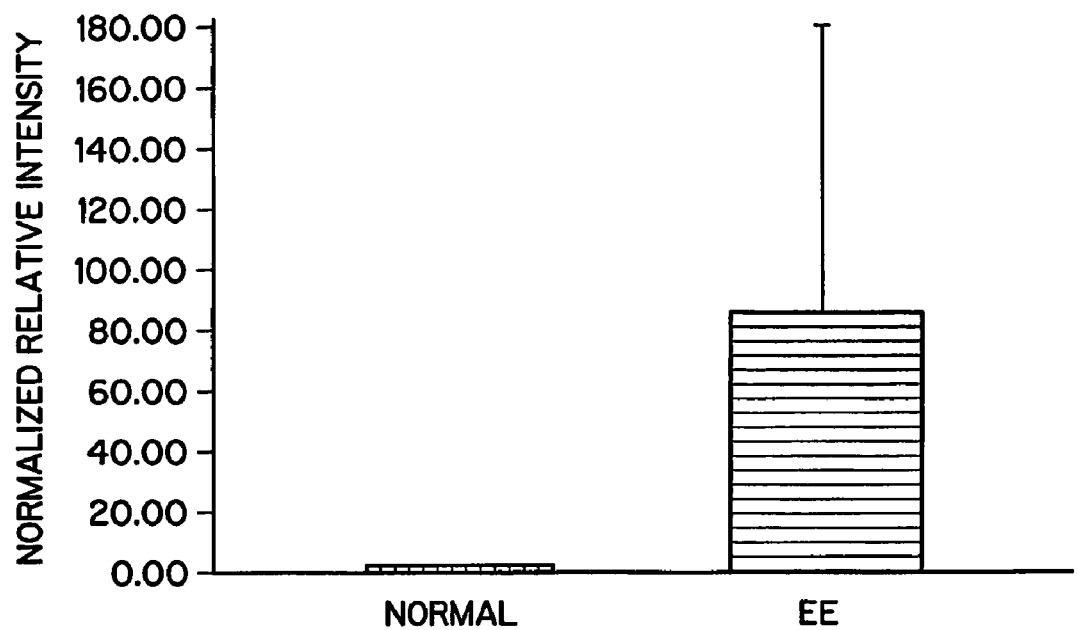
FIG. 1 shows DNA microarray data of eotaxin-3 mRNA levels in esophageal tissue of normal patients and patients with eosinophilic esophagitis (EE).

Methods of diagnosing, assessing, and mitigating eosinophilic esophagitis by modulating levels and activity of eotaxin-3 are disclosed.

Eotaxin-3 is a CC chemokine with selective activity on eosinophils. For example, eotaxin-3 recruits and directs eosinophils to sites in the body, such as the esophagus, via chemoattraction. Additional chemokines have been identified in the genome that encode for CC chemokines with eosinophil-selective chemoattractant activity, and have been designated eotaxin-1 and eotaxin-2.

The activity of eotaxin-3 is mediated by the selective expression of an eotaxin receptor, CCR3, on eosinophils. CCR3 is a promiscuous receptor; it interacts with multiple ligands including macrophage chemoattractant proteins (MCP)-2, -3, and -4, RANTES (regulated upon activation normal T-cell expressed and secreted), and HCC-2 (MIP-5, leukotactin). The only ligands that signal exclusively through this receptor, however, are eotaxins-1, -2, and -3, accounting for the cellular selectivity of the eotaxins.

Esophageal tissue obtained from patients previously diagnosed with eosinophilic esophagitis was analyzed. Diagnosis was based on analysis of excised tissue from endoscopic biopsy. Tissues from patients with eosinophilic esophagitis, as well as patients not having eosinophilic esophagitis (controls) were subjected to genome-wide microarray transcript profiling (Affymetrix GeneChip). All work was performed at the Core facility at Children's Hospital Medical Center (Cincinnati, Ohio).

Briefly, RNA quality was first assessed using the Agilent Bioanalyzer (Agilent Technologies, Palo Alto Calif.). Only mRNA having a ratio of 28S/18S between 1.3 and 2 were subsequently used. RNA was converted to cDNA with Superscript choice for cDNA synthesis (Invitrogen, Carlsbad Calif.) and subsequently converted to biotinylated cRNA with Enzo High Yield RNA Transcript labeling kit (Enzo Diagnostics, Farmingdale N.Y.). After hybridization to the GeneChip (Affymetrix, Santa Clara Calif.), the chips were automatically washed and stained with streptavidin-phycoerythrin using a fluidics system. The chips were scanned with a Hewlett Packard GeneArray Scanner. Over 30,000 unique genes were screened.

Levels of gene transcripts were determined from data image files, using algorithms in the Microarray Analysis Suite software (Affymetrix). Levels from chip to chip were compared by global scaling; thus, each chip was normalized to an arbitrary value (1500). Each gene is typically represented by a probe set of 16 to 20 probe pairs. Each probe pair consists of a perfect match oligonucleotide and a mismatch oligonucleotide that contains a one base mismatch at a central position. Two measures of gene expression were used, absolute call and average difference. Absolute call is a qualitative measure in which each gene is assigned a call of present, marginal or absent, based on the hybridization of the RNA to the probe set. Average difference is a quantitative measure of the level of gene expression, calculated by taking the difference between mismatch and perfect match of every probe pair and averaging the differences over the entire probe set. Data were normalized and gene lists were created with results having $p<0.05$ and >2-fold change.

FIG. 1 shows the normalized relative average difference of the gene encoding eotaxin-3 from normal patients and patients with eosinophilic esophagitis. The microarray analysis identified eotaxin-3 as the top gene induced, indicating a role in eosinophilic esophagitis. Eotaxin-1 and eotaxin-2 mRNA levels were not significantly increased in eosinophilic esophagitis patients.

Figure 2:
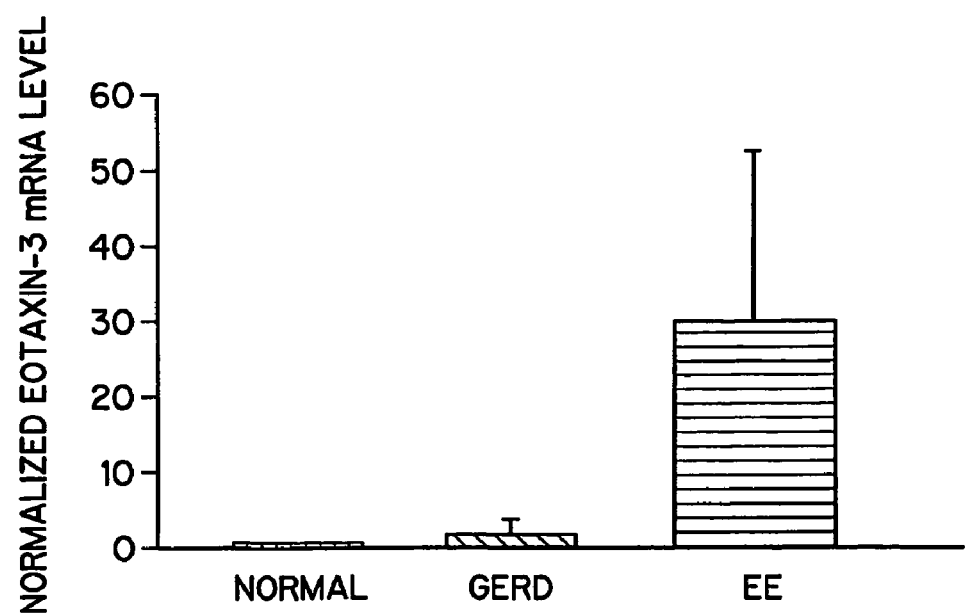
FIG. 2 shows data from quantitative polymerase chain reaction analysis showing normalized eotaxin-3 mRNA levels in normal patients, patients with gastroesophageal reflux disease (GERD), and patients with eosinophilic esophagitis.

Quantitative polymerase chain reaction (PCR) using LightCycler technology (Roche Diagnostics Corp. Indianapolis, Ind.) which involves a competitive amplification of cDNA prepared from esophageal RNA, known to one skilled in the art, was further utilized to validate the microarray analysis results. Levels of eotaxin-3 mRNA from normal patients, patients with gastroesophageal reflux disease (GERD), and patients with eosinophilic esophagitis were compared. As shown in FIG. 2, eotaxin-3 mRNA was induced nearly 100-fold in patients with eosinophilic esophagitis when normalized to a housekeeping gene GAPDH. Patients with GERD showed only slightly increased levels compared to normal patients. Levels of the other two eotaxin mRNA species (eotaxin-1 and eotaxin-2) were not increased in patient esophageal samples (data not shown), validating the specific role of eotaxin-3.

A murine model of eosinophilic esophagitis was evaluated to determine the role of the eotaxin-3 receptor, CCR3. The model is disclosed in Mishra et al., *J. Clin. Invest.* (2001) 107, 83, which is expressly incorporated by reference herein in its entirety. Because eosinophilic esophagitis is marked by infiltration of eosinophils, this condition may be linked to exposure to allergens. In support of this, animals models of eosinophilic esophagitis were induced by allergen exposure to the respiratory tract. In brief, mice were exposed to repeated doses of intranasal *Aspergillus fumigatus* antigen (three doses every 48 hours/week) for three weeks. Subsequently, the mice were euthanized 18 hours after the last dose of allergen or saline control, and the esophagus was analyzed for the occurrence of eosinophilic esophagitis.

Figure 3:
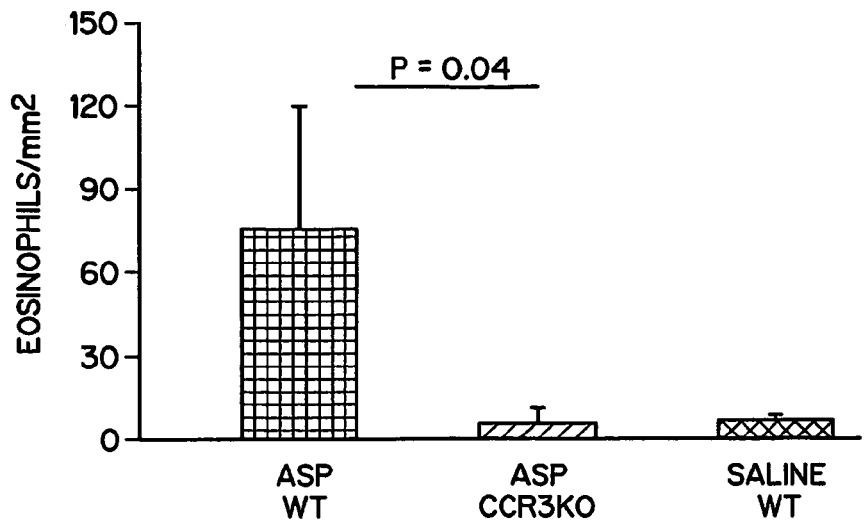
FIG. 3 shows esophageal eosinophil concentration in control and allergen-induced wild-type mice, and allergen-induced mice lacking the gene encoding the CCR3 receptor.

Specifically, asthma was experimentally induced in wild-type and CCR3 knockout (KO) mice (a gift of Drs. Craig Gerard and Allison Humbles at Harvard Medical School) using *Aspergillus fumigatus* (ASP) as an allergen. Wild-type control mice received saline. The concentration of eosinophils was determined in the esophagus of allergen-induced wild-type mice (ASP wt), control wild-type mice (saline wt), and allergen-induced mice lacking the gene encoding CCR3 (ASP CCR3KO). The results are shown in FIG. 3.

The concentration of eosinophils in allergen-induced wild-type mice (ASP wt) was about 75 eosinophils per $mm^2$. The concentration of eosinophils in allergen-induced CCR3KO mice (ASP CCR3KO) was about 4 eosinophils per $mm^2$, similar to the eosinophil concentration in control wild-type mice (saline wt). The decreased concentration of eosinophils in allergen-induced CCR3KO mice compared to allergen-induced wild-type mice was statistically significant ($p=0.04$; Students T-test).

Eosinophilic esophagitis related symptoms and/or pathology may be mitigated by mediating eosinophil chemotactic events using techniques such as those disclosed in U.S. Pat. No. 6,780,973, which is expressly incorporated by reference herein in its entirety. One example is a recombinant polypeptide capable of mediating eosinophil chemotactic events where the polypeptide includes a domain having a sequence which has at least 70% identity to full length murine eotaxin cDNA, full length guinea pig eotaxin cDNA, and/or human eotaxin DNA. Another example is reducing eotaxin activity using an antagonist such as an anti-eotaxin-3 antibody or eotaxin-1, -2, or -3 fragment, a purified antibody which binds specifically to a murine or human eotaxin-3 protein including an intact monoclonal or polyclonal antibody, an immunologically active antibody fragment, or a genetically engineered fragment. The antagonist may be an eotaxin-1, -2, or -3 polypeptide having a deletion of 1-10 N-terminal amino acids, or having an addition of 3-10 amino acids on the amino terminus.

The concentration of eotaxin-3 protein in plasma was elevated in patients with eosinophilic esophagitis, compared to normal controls. Concentrations were determined using a commercially purchased sandwich ELISA kit (R&D Quantikine CCL-26 kit, R&D Systems Inc., Minneapolis, Minn.). In blood anticoagulated with heparin, eotaxin-3 concentrations in plasma of normal patients were 29.43 pg/ml±15.4 pg/ml (n=6), and eotaxin-3 concentration in patients with eosinophilic esophagitis were 52.97 pg/ml±12 pg/ml (n=3)

Figure 4:
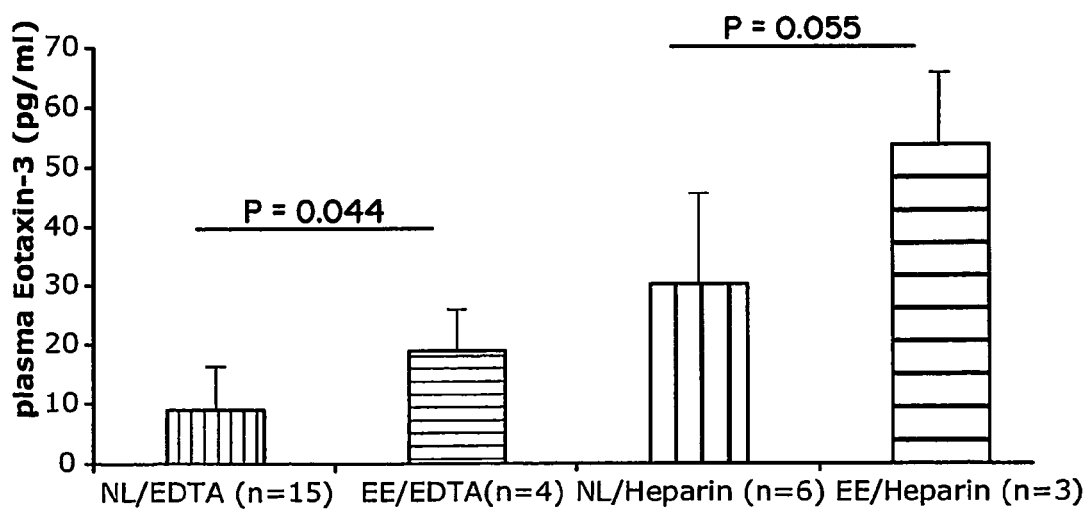
FIG. 4 shows plasma concentrations of eotaxin-3 in normal patients and patients with eosinophilic esophagitis.

(p=0.055). In blood anticoagulated with ethylenediamine tetraacetic acid (EDTA), eotaxin-3 concentrations in plasma of normal patients were 8.3 pg/ml+7 pg/ml (n=15), and eotaxin-3 concentration in patients with eosinophilic esophagitis were 18.19 pg/ml±7 (n=4) (p=0.044). These data are shown in FIG. 4.

Therefore, the blood concentration of eotaxin-3 in an individual may be compared to a normal level as a relatively non-invasive or minimally invasive indication of eosinophilic esophagitis. In one embodiment, a plasma concentration of eotaxin-3 of about 52.97 pg/ml±12 pg/ml in blood anticoagulated with heparin is indicative of eosinophilic esophagitis. In another embodiment, a plasma concentration of eotaxin-3 of about 18.19 pg/ml±7 pg/ml in blood anticoagulated with EDTA is indicative of eosinophilic esophagitis. These blood concentrations of eotaxin-3 may serve as a diagnostic marker, for which a less invasive diagnostic test for eosinophilic esophagitis may be used, as further discussed below, to replace or serve as a preliminary indicator or whether a more invasive test, e.g. endoscopic biopsy, is warranted. The level of eotaxin-3 may also serve to determine if a specific therapy is mitigating eosinophilic esophagitis, and thus may be used to monitor therapy. Similarly, the concentration or amount of eotaxin-3 DNA, eotaxin-3 mRNA, or eotaxin-3 protein over a normal amount in a patient tissue, such as blood or esophageal tissue, can be utilized further as an indicator of eosinophilic esophagitis in the patient.

In one embodiment, a diagnostic assay for eosinophilic esophagitis includes an ELISA (enzyme linked immunosorbent assay) or other clinically applicable immunoassay. In another embodiment, a diagnostic assay for eosinophilic esophagitis includes a test strip containing an anti-eotaxin-3 antibody to which eotaxin-3 in a patients biological sample (e.g. blood, sputum, feces, tissue fluid, cerebrospinal fluid, etc.) would bind. The test strip may include a chromogenic, fluorogenic, or luminescent substrate, detection reagents, etc., as known to one skilled in the art. The anti-eotaxin-3 antibody may be a rodent or other animal anti-eotaxin-3 antibody. The assay would include at least one suitable reagent, such as an enzyme (e.g. an oxidoreductase, transferase, hydrolase, lyase, isomerase, or ligase), in one embodiment horseradish peroxidase, o-toluidine, or colloidal gold, whereby the reagent reacts with an antigen/antibody complex on the test strip. A chromogen or other detectable indicator of binding or lack of binding, depending upon the assay format (e.g. competitive, non-competitive, sandwich, etc.) indicates binding of the anti-eotaxin-3 antibody to eotaxin-3 present in a supranormal level for a qualitative test, and may indicate the degree of binding for a quantitative or semi-quantitative test. Binding typically is indicated or visually detected via the presence or absence of color, fluorescence, luminescence, etc. Such test kit components and configurations are well known to one skilled in the art and are within the scope of the invention.

An example of certain suitable substrates and a suitable reagent may include, respectively, dimethyl or diethyl analogues of p-phenylenediamine with 4-chloro-1-naphthol or 3-methyl-2-benzothiazoline hydrazone with 4-chloro-1-naphthol and horseradish peroxidase. Other exemplary substrates used with horseradish peroxidase include 3,3',5,5'-tetramethylbenzidine, 2,2'-azinobis[3-ethylbenzothiazoline-6-sulfonic acid]-diammonium salt, o-phenylenediamine dihydrochloride, and QuantaBlu.

The anti-eotaxin-3 antibody may be a monoclonal or polyclonal antibody. Methods of producing monoclonal and polyclonal antibodies are known to one skilled in the art. Anti-eotaxin-3 antibodies may be generated as disclosed in U.S. Pat. No. 6,780,973, previously expressly incorporated by reference herein in its entirety. Also, a commercially available anti-eotaxin-3. antibody may be used.

As indicated above, eotaxin-3 selectively signals through the CCR3 receptor expressed on activated eosinophils or on other cells such as mast cells. As such, eosinophilic esophagitis may be mitigated by altering an eotaxin-3 binding and/or signaling mechanism, and/or CCR3 structure, function, and/or internalization. One such example is a method to provide an inhibitor to eotaxin-3 and/or CCR3 in an eosinophil or a mast cell under conditions sufficient to inhibit eotaxin-3 binding to the receptor. For example, the inhibitor may be provided to the esophageal tissue or to the blood stream in an amount sufficient to inhibit eotaxin-3 binding to the eotaxin-3 receptor. The inhibitor may be a small molecule inhibitor and/or a CCR3 antagonist. Exemplary CCR3 antagonists may include a humanized or human anti-eotaxin-3 antibody, MIG, I-TAC, IP-10 (U.S. patent application Ser. No. 10/752,659, titled "Cytokine Inhibition of Eosinophils," filed on Jan. 7, 2004; Zimmerman et al., *J. Allergy Clin. Immunol.*, (2003) 3, 227), vMIP-II (Kleidel et al., *Science*, (1997) 277, 1656), met-RANTES (Elsner et al., *Eur. J. Immunol.*, (1997) 27, 2892), carboxamide derivatives (Naya et al., *Bioorg. Med. Chem. Lett.*, (2001) 11, 1219), 2-(Benzothiazolylthio)acetamide derivatives (Naya et al., *Chem. Pharm. Bull.*, (2003) 51, 697; Saeki et al., *Biochem. Biophys. Res. Comm.*, (2001) 281, 779), piperidine derivatives including indolinopiperidines or benzylpiperidines (Wacker et al., *Bioorg. Med. Chem. Lett.*, (2002) 12, 1785; Varnes et al., *Bioorg. Med. Chem. Lett.*, (2004) 14, 1645), or such other nonpeptides as UCB35625 and derivatives thereof (Sabroe et al., *J. Biol. Chem.*, (2000) 275, 25985), and SK&F-$_L$-45523 and derivatives thereof (White et al., J. Biol. Chem, (2000) 275, 36626). Certain of the above antagonists, e.g., UCB35625, may also be considered small molecule inhibitors (Sabroe et al., *J. Biol. Chem.*, (2000) 275, 25985). Each of the references cited is expressly incorporated by reference herein in its entirety.

The inhibitor need not completely inhibit binding, signal transduction, and/or function or cause receptor internalization. As used herein, an inhibitor may cause any reduction in one or more of these properties compared to a normal level. An eotaxin-3 and/or CCR3 inhibitor may also specifically inhibit transcription and/or translation of eotaxin-3, and/or CCR3 such as by utilizing antisense oligonucleotides and transcription factor inhibitors. An inhibitor may include a glucocorticoid that can work by inhibiting eotaxin-3 promoter-driven reporter gene activity and accelerating the decay of eotaxin-3 mRNA (Zimmerman et al., *J. Allergy Clin. Immunol.*, (2003) 3, 227). An inhibitor may also induce CCR3 initialization (Zimmermann et al., *J. Biol. Chem.*, (1999) 274, 12611). Each of the references cited is expressly incorporated by reference herein in its entirety.

An inhibitor may be administered directly or with a pharmaceutically-acceptable diluent, carrier, or excipient, in unit dosage form. Conventional pharmaceutical practice may be employed to provide suitable formulations or compositions to administer the inhibitor to patents with, or presymptomatic for, eosinophilic esophagitis. Any appropriate route of administration may be employed, for example, parenteral, intravenous, subcutaneous, intramuscular, intracranial, intraorbital, ophthalmic, intraventricular, intracapsular, intraspinal, intracisternal, intraperitoneal, intranasal, aerosol, or oral administration. Therapeutic formulations may be in the form of solids, liquid solutions, or suspensions; for oral administration, formulations may be in the form of tablets (chewable, dissolvable, etc.), capsules (hard or soft gel), pills, syrups, elixirs, emulsions, etc.; and for intranasal formulations, in the form of powders, nasal drops, or aerosols. In one embodiment, a CCR3 antagonist is administered parenterally and/or orally. Enteral formulations may contain thixotropic agents, flavoring agents, and other ingredients for enhancing organoleptic qualities.

Methods known in the art for making formulations are found in, for example, "Remington's Pharmaceutical Sciences." Formulations for parenteral administration may, for example, contain excipients, including but not limited to pharmaceutically acceptable buffers, emulsifiers, surfactants, and electrolytes such as sodium chloride, as well as sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Formulations for inhalation may also contain excipients, for example, lactose, or may be aqueous solutions containing, for example, polyoxyethylene-lauryl ether, glycocholate and deoxycholate, or may be oily solutions for administration in the form of nasal drops, or as a gel.

Other variations or embodiments of the invention will also be apparent to one of ordinary skill in the art from the above figures and descriptions. Thus, the forgoing embodiments are not to be construed as limiting the scope of this invention.

What is claimed is:

1. A diagnostic method for eosinophilic esophagitis, comprising:
   providing a sample from a patient suspected of having eosinophilic esophagitis, wherein the sample comprises blood anticoagulated with heparin;
   detecting, from the patient sample, an elevated level of eotaxin-3 protein, wherein the level of eotaxin-3 protein in the patient sample is at least about 20 pg/mL or higher than the level of eotaxin-3 protein in a normal sample; and
   diagnosing eosinophilic esophagitis in the patient based on the presence of the elevated level of eotaxin-3 protein in the patient sample.

2. A diagnostic method for eosinophilic esophagitis, comprising:
   providing a sample from a patient suspected of having eosinophilic esophagitis, wherein the sample comprises blood anticoagulated with EDTA;
   detecting, from the patient sample, an elevated level of eotaxin-3 protein, wherein the level of eotaxin-3 protein in the patient sample is at least about 8 pg/mL or higher than the level of eotaxin-3 protein in a normal sample; and
   diagnosing eosinophilic esophagitis in the patient based on the presence of the elevated level of eotaxin-3 protein in the patient sample.

3. The diagnostic method of claim 1 or claim 2, further comprising:
   applying the patient sample to an anti-eotaxin-3 antibody and at least one reagent, wherein the at least one reagent, when combined with the anti-eotaxin-3 antibody, indicates the presence or absence of binding between eotaxin-3 and anti-eotaxin-3 antibody, and
   determining the level of binding of the anti-eotaxin-3 antibody with eotaxin-3 present in the patient sample, wherein an elevated level of binding indicates an elevated level of eotaxin-3 protein.

4. The diagnostic method of claim 3, further comprising:
   reacting, in both the patient sample and normal sample, the at least one reagent with a chromogenic, fluorogenic, or luminescent substrate, wherein the presence of a stronger signal in the patient sample than that in the normal sample indicates binding of the anti-eotaxin-3 antibody to eotaxin-3 present in an elevated level in the patient sample.

5. The diagnostic method of claim 3, wherein the at least one reagent comprises an enzyme selected from the group consisting of an oxidoreductase, a transferase, a hydrolase, a lyase, an isomerase, and a ligase.

6. The diagnostic method of claim 3, wherein the anti-eotaxin-3 antibody is a purified antibody which binds to a murine or human eotaxin-3protein, and wherein the anti-eotaxin-3 antibody is selected from the group consisting of an intact monoclonal antibody, a polyclonal antibody, and an immunologically active antibody fragment.

7. The diagnostic method of claim 3, wherein an ELISA device or a test strip is used to contain the anti-eotaxin-3 antibody and the reagent.

* * * * *

UNITED STATES PATENT AND TRADEMARK OFFICE
CERTIFICATE OF CORRECTION

PATENT NO. : 8,030,003 B2
APPLICATION NO. : 11/721127
DATED : October 4, 2011
INVENTOR(S) : Marc E. Rothenberg Page 1 of 1

It is certified that error appears in the above-identified patent and that said Letters Patent is hereby corrected as shown below:

Column 1, lines 9-13; delete "The U.S. Government has a paid-up license in this invention and the right in limited circumstances to require the patent owner to license others on reasonable terms as provided for by the terms of Grant No. 2R01 AI045898-05 awarded by the National Institutes of Health." and insert --This invention was made with U.S. Government support on behalf of Grant No. 2R01 AI045898-05 awarded by the National Institutes of Health. The U.S. Government has certain rights in this invention.--

Signed and Sealed this
Ninth Day of April, 2013

Teresa Stanek Rea
*Acting Director of the United States Patent and Trademark Office*

UNITED STATES PATENT AND TRADEMARK OFFICE
CERTIFICATE OF CORRECTION

| | | |
|---|---|---|
| PATENT NO. | : 8,030,003 B2 | Page 1 of 1 |
| APPLICATION NO. | : 11/721127 | |
| DATED | : October 4, 2011 | |
| INVENTOR(S) | : Marc E. Rothenberg | |

It is certified that error appears in the above-identified patent and that said Letters Patent is hereby corrected as shown below:

In the Specifications

Column 1, lines 9-13; delete "This invention was made with U.S. Government support on behalf of Grant No. 2R01 AI045898-05 awarded by the National Institutes of Health. The U.S. Government has certain rights in this invention." and insert --This invention was made with government support under AI045898 awarded by the National Institutes of Health. The government has certain rights in the invention.--

Signed and Sealed this
Eighteenth Day of February, 2014

Michelle K. Lee
*Deputy Director of the United States Patent and Trademark Office*